US012768828B2

(12) United States Patent
Da Silva et al.

(10) Patent No.: US 12,768,828 B2
(45) Date of Patent: Oct. 20, 2026

(54) COMPOSITION FOR IDENTIFYING THE ORIGIN OF SCALE, PROCESS FOR PREPARING SAID COMPOSITION AND PROCESS FOR IDENTIFYING THE ORIGIN OF SCALE USING SAID COMPOSITION

(71) Applicant: PETRÓLEO BRASILEIRO S.A.—PETROBRAS, Rio de Janeiro RJ (BR)

(72) Inventors: Mario Germino Ferreira Da Silva, Rio de Janeiro (BR); Fatima Andreia De Freitas Brazil, Rio de Janeiro (BR)

(73) Assignee: PETRÓLEO BRASILEIRO S.A.—PETROBRAS, Rio de Janeiro (BR)

(*) Notice: Subject to any disclaimer, the term of this patent is extended or adjusted under 35 U.S.C. 154(b) by 468 days.

(21) Appl. No.: 18/394,658

(22) Filed: Dec. 22, 2023

(65) Prior Publication Data

US 2024/0210376 A1 Jun. 27, 2024

(30) Foreign Application Priority Data

Dec. 23, 2022 (BR) .......................... 1020220265763

(51) Int. Cl.
*G01N 33/28* (2006.01)

(52) U.S. Cl.
CPC ................................ *G01N 33/2823* (2013.01)

(58) Field of Classification Search
CPC ......... C09K 8/426; C09K 8/528; E21B 47/11; G01N 33/2823
See application file for complete search history.

(56) References Cited

U.S. PATENT DOCUMENTS

2016/0272882 A1 9/2016 Stray et al.

FOREIGN PATENT DOCUMENTS

| | | | | | |
|---|---|---|---|---|---|
| BR | 112014012122 | A2 | | 6/2017 | |
| JP | 2004022633 | A | * | 1/2004 | ............... G01C 9/02 |
| WO | WO-2023114893 | A1 | * | 6/2023 | ............... C09K 8/70 |

OTHER PUBLICATIONS

Corbett et al., Radon tracing of groundwater input into Par Pond, Savannah River Site. Journal of Hydrology. 1997;203:209-227.

Hu et al., Streamline Simulation of Barium Sulfate Precipitation Occurring Within the Reservoir Coupled With Analysis of Observed Produced-Water-Chemistry Data to Aid Scale Management. SPE International Oilfield Scale Conference and Exhibition. 174235, 17 pages, (2017).

Ramstad et al., The Johan Sverdrup Field: Origin of Sulfate-Rich Formation Water and Impact on Scale Management Strategy. SPE International Oilfield Scale Conference and Exhibition. 179895, 13 pages, (2016).

Stamatakis et al., Study of Calcium Carbonate Precipitation in the Near-Well Region Using 47Ca as Tracer. SPE International Oilfield Scale Conference and Exhibition. 87436, 7 pages, Feb. 2006.

* cited by examiner

*Primary Examiner* — Anthony J Green
(74) *Attorney, Agent, or Firm* — McCarter & English, LLP; Wei Song

(57) ABSTRACT

The present invention relates to the composition of calcite impregnated with chemical tracer, process for obtaining the same and process for identifying the origin of scale through mapping the tracer incorporated in the calcite, which is added to a viscous gel-based mattress. The present invention further comprises the use of said composition to identify the source of calcium carbonate scale in a well. Thus, it is possible to verify whether the origin of the calcium carbonate in the scale formed in the production column comes from the material injected into the well. Once this occurrence is confirmed, it is possible to plan ways to mitigate scale formation through material to combat circulation loss, thus avoiding production losses associated with scale formation.

16 Claims, 3 Drawing Sheets

(A) (B) (C)

COMPOSITION FOR IDENTIFYING THE ORIGIN OF SCALE, PROCESS FOR PREPARING SAID COMPOSITION AND PROCESS FOR IDENTIFYING THE ORIGIN OF SCALE USING SAID COMPOSITION

RELATED APPLICATIONS

This application claims the benefit of priority to Brazilian Patent Application No. 1020220265763, filed Dec. 23, 2022, the entire contents of which are incorporated herein by reference.

FIELD OF THE INVENTION

The present invention relates to the composition of calcite impregnated with chemical tracer, process for obtaining the same and process for identifying the origin of scale through mapping the tracer incorporated into the calcite, which is added to a viscous gel-based mattress. The invention further comprises the use of said composition to identify the source of calcium carbonate scale.

The present invention falls within the technical field of drilling and completing wells, oil production processes and lifting and flow technologies. More specifically, the field of application is in the areas of reservoir management, scale management as well as lifting and drainage to ensure production flow.

BACKGROUND OF THE INVENTION

During the drilling of oil wells there is always the possibility of circulation loss of drilling fluid to the formations being drilled. This circulation loss can be avoided by controlling the perforation. In this sense, it is important to highlight that the balance of fluid circulation within the well occurs when the fluid pumped into the well is able to return to the surface, thus carrying the cuttings generated in the drilling process. In other words, thus cleaning the well by removing rock fragments (gravels) that are removed by the action of the fluid flow injected by pumping inside the drill string, passing through the drill jets and returning through the annulus between the well walls and drill string. When the fluid injected into the column returns to the surface through the annulus, it carries the cuttings produced during drilling. Circulation loss occurs when the drilling fluid is unable to form grout on the well wall, normally due to the presence of faults or fractures. The circulation loss generates a lowering of the fluid level in the well, due to the entry of drilling fluid into the reservoir, thus the hydrostatic pressure (column pressure) inside the well is lower than the static pressure (pressure of the well formation) of the reservoir.

In the Pre-salt reservoir, for example, it was identified that the circulation loss is related to the inability of the drilling fluid to seal sections with high porosity and permeability associated with dissolution (intervals with widened fractures and cavities/caves, for example).

Consequently, the hydrostatic pressure of the mud column must be maintained at a value high enough to prevent the flow of formation fluid into the well, which could result in problems such as kick and even a blowout. The kick would represent the unwanted influx of fluids present in the formation (water, gas or oil) into the well, due to the existence of a hydrostatic pressure inside the well that is insufficient to contain the formation pressure. When it occurs in an uncontrolled manner and reaches the surface, it is called a blowout.

The reestablishment of well drilling control, after the beginning of the fluid circulation loss, occurs with the pumping of mattresses to combat circulation loss, these being made up of viscous mattresses (made of organic polymers) with calcite (calcium carbonate) in different particle sizes (fine, medium and coarse), where the polymers can be xanthan gum and cellosize in the concentration range of 1.5 lb/bbl (pound per barrel). This material to combat circulation loss is pumped into the well and displaced through the fluid in the well drilling phase. The same phenomenon can also occur in the completion phase, with the flow rate of the viscous mattress in surface equipment normally being in a range between 5 and 20 BPM (barrels per minute).

This mixture of plugging materials of different calcite granulometry with the viscous mattress works as a buffering agent for the formation, thus creating grouting structures that function as temporary sealants to the flow of fluid loss, from the well wall even inside the reservoir (including heterogeneities related to dissolution), interrupting the circulation loss and reestablishing control of the fluid level inside the well.

Currently, during well production, even in a situation of low BSW (Bottom Sediments Water—produced water), in a range of around 0.2% to 0.5%, the formation of inorganic scale occurs in the production column wells, thus impacting production. This scale generates loss of production due to partial blockage of the production column due to the reduction in its diameter. In this sense, it is noteworthy that the calcium carbonate that is forming in this scale during production may originate from the reservoir rock, the formation water or materials injected during loss control (during drilling or well completion). Given this context, the technical problem that motivated the invention was the need to identify the origin of the material that is forming the scale in the production columns.

The solution found to identify the origin of the calcium carbonate precipitated in the scale inside the production column was mapping through the use of chemical tracers incorporated into the calcite, which would be added to the viscous gel-based mattresses. In this way, it is possible to track whether the carbonate precipitated in the scale comes from materials injected during loss control (during drilling or well completion).

The state of the art discloses the use of tracers, as a technology in the field of reservoirs, to chemically mark, for example, the moment in which a water front arrives at the producing well after being injected into an injection well and crossing the said reservoir. The identification of tracers is carried out through chemical analysis of the water produced by the producing wells, in this way, it is possible to identify, through the arrival of the tracers, which producing wells are receiving water from the injection well. Thus, it becomes possible to calculate the time it took to cross the distance between the injection well and the producer, as well as knowing whether the tracer is reaching other producing wells, thus being able to measure the efficiency of the reservoir sweep.

Chemical tracers of non-radioactive compounds, such as: iodides (e.g.: potassium iodide), bromides (e.g.: potassium bromide), alkali metal halides were mentioned in the literature for monitoring phenomena in reservoirs, but have not been described for the purpose of the present invention (such as Chrysikopoulos, C. V.; Kruger P.; Chelated Indium Activable Tracers for Geothermal Reservoirs, SGP-TR-99, Stanford University: California, 1986). Alkali metal halides have potential reactivity and high detection limits. Despite the high detection limits, the low cost of the non-radioactive material allows the injection of large amounts, compensating for the sensitivity of the method. The analysis of chemical tracers can be carried out using high-performance liquid chromatography, nuclear magnetic resonance and mass spectrometry. Bromides and fluorobenzoic acids (FBAs) are applicable in the study of environmental processes such as mass transport processes (as disclosed in Corbert, D. R.; Burnett. W. C.; Cable, P. H.; Clark, S. B.; J. Hydrol. 1997, 203, 209), but were not described for the purpose of the present invention.

Regarding the current state of the art in this area, the document entitled "Study of Calcium Carbonate Precipitation in the Near-Well Region Using 47Ca as Tracer" is a study on the precipitation of calcium carbonate in the oil well region, using 47Ca as a radioactive tracer. FIG. 2 of this document shows equipment used at laboratory scale to analyze scale formation using precipitation induction time. The aforementioned document proposes a method for evaluating the formation of calcium carbonate scale based on samples of porous materials ("sand-pack") and laboratory equipment (shown in FIG. 2) instead of using the tracer in the field. Therefore, said article departs from the present invention because it is not related to the proposed solution and because it uses a radioactive and non-chemical tracer.

The document entitled "The Johan Sverdrup Field: Origin of Sulfate-Rich Formation Water and Impact on Scale-Management Strategy" deals with an oil field located in Norway and the formation of scales of strontium sulfate, calcium carbonate and barium sulphate. This article disclosed the importance of analysis of formation water, injection of seawater, reinjection of produced water and injection of low salinity/low sulfate water, in the formation of these scales during the production and non-drilling stage. Therefore, said research departs from the present invention, whose objective is to identify only calcium carbonate scale through the use of chemical tracers, collecting the material as well as reestablishing control of the drilling and production column.

The document entitled "Streamline Simulation of Barium Sulfate Precipitation Occurring Within the Reservoir Coupled With Analyzes of Observed Produced-Water-Chemistry Data To Aid Scale Management" deals with the analysis of produced water and formation of scale, such as barium sulfate, strontium sulfate, calcium sulfate. Therefore, said document departs from the present invention as it does not relate to calcium carbonate scale, as in the present invention. Furthermore, the present invention does not analyze the water produced in its method.

The document BR 112014012122-2 discloses methods for fracturing a well, controlling sand and monitoring well production, in sandstone or carbonate reservoirs. One of the essential features of this document is the use of a controlled release tracer, unlike the present invention which uses a chemical tracer, wherein the tracer is a component of the hydraulic fracturing operation. Furthermore, the present invention discloses a method of identifying calcium carbonate scale through the use of chemical tracers, collecting the material as well as reestablishing control of well drilling and production. The present invention also does not use controlled release, only chemical labeling with tracers.

The North American document US 2016/272882 relates to the use of chemical tracers to monitor the production of oil wells, in order to measure flow, pH and salinity. However, this document does not disclose a method of identifying calcium carbonate scale. Furthermore, the chemical tracer described in the present invention is much simpler, unlike the document, where there is a need for controlled release and inclusion in crystals.

As can be seen, none of the documents present the solution proposed in the present invention of identifying calcium carbonate scale through the use of chemical tracers, collecting the material as well as reestablishing control of the well drilling and production column during the productive life of the well.

SUMMARY OF THE INVENTION

The present invention discloses a calcite composition impregnated with chemical tracer with a viscous mattress used during well construction and in operations to combat circulation loss, in order to verify the influence of this calcite on the formation of scale in the production phase from the well. This composition aims to identify calcium carbonate scales through the use of chemical tracers, collecting the material as well as reestablishing well drilling control (combating circulation loss) and also production during the productive phase (where samples are analyzed to check whether there is a trace of the tracer).

The use of calcite impregnated with chemical tracer also aims to increase the future efficiency of the process of inhibiting scale formation in the production system by identifying the origin of the calcite deposited in the production column.

BRIEF DESCRIPTION OF THE FIGURES

The present invention will be described below, with reference to the attached figures which, in a schematic way and not limiting the inventive scope, represent examples of its implementation.

DETAILED DESCRIPTION OF THE INVENTION

Figure 1:
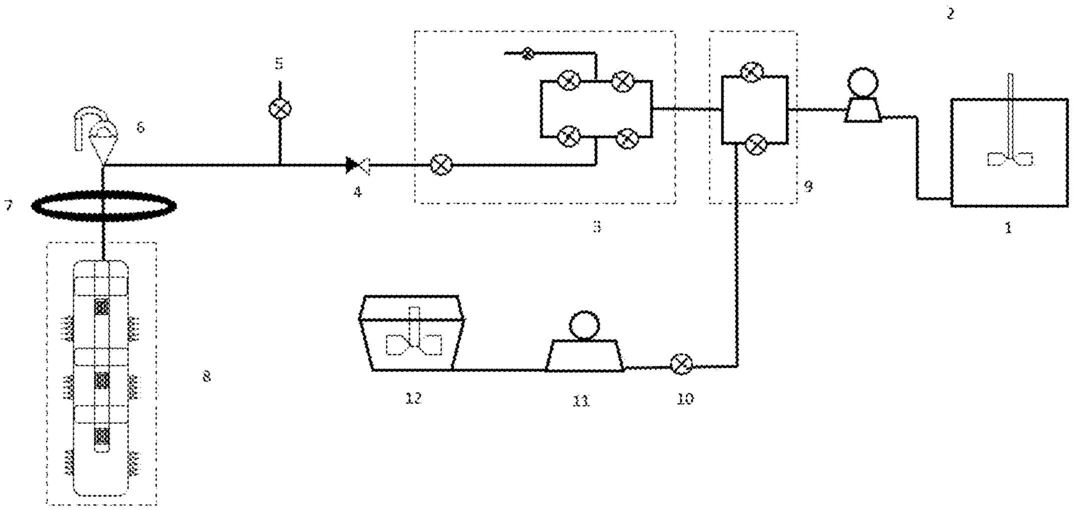
FIG. 1 illustrates the scheme that represents the circulation system, pumping system of the completion rig, taking advantage of the rig tanks for preparation and injection of the mattress to combat circulation loss in the sea well during the operation to combat circulation loss. The constituent units of the scheme are fluid supply tank (1); probe pump (2); Standpipe manifold (3); Check valve (4); relief line (5); injection head (6); rotary table (7); well diagram (8); manifold (9); valve (10); pumping skid (11) and batch mix (12).
Figure 2:
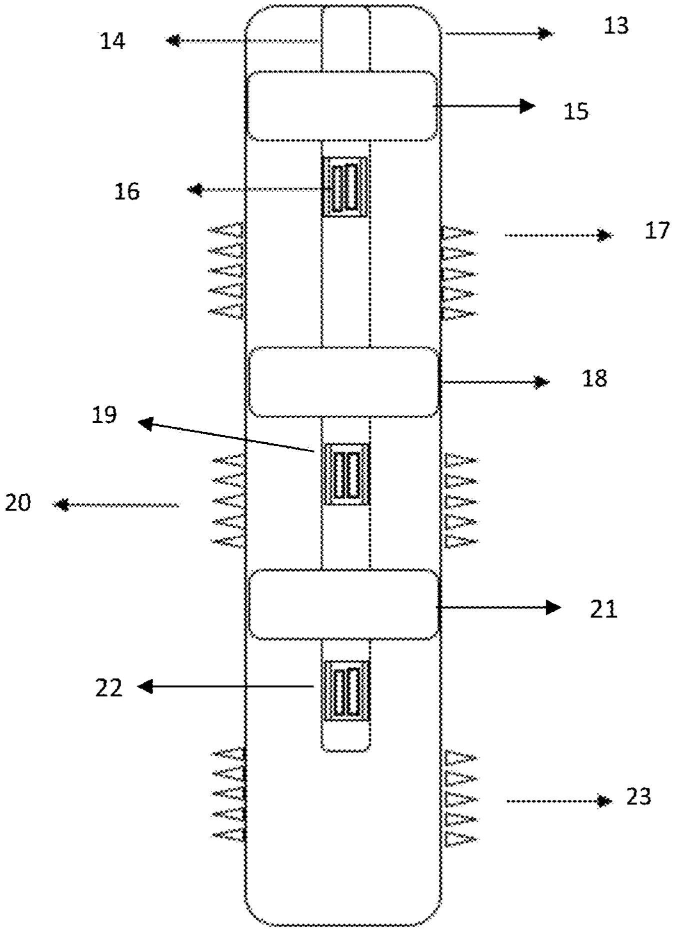
FIG. 2 represents the detailed well scheme, present in FIG. 1. The constituent units of the scheme are well casing (13); production column (14); upper packer (15); top flow valve (16); cannonades from the upper range (17); intermediate packer (18); Intermediate flow valve (19); cannonades from the intermediate range (20); lower packer (21); lower flow valve (22); cannonades from the lower range (23).
Figure 3:
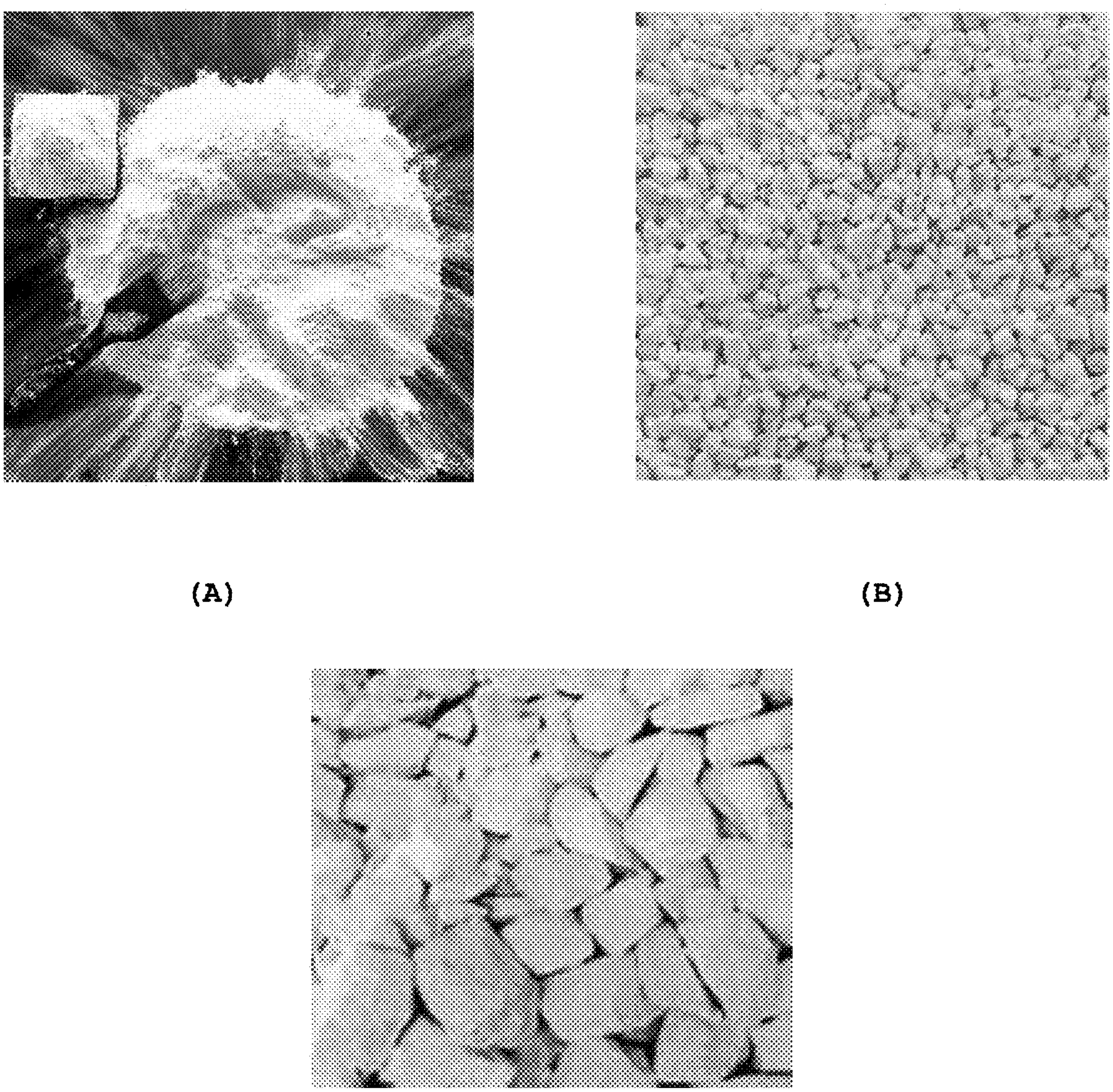
FIG. 3 illustrates the granulometry of fine (A), medium (B) and coarse (C) calcites.

The present invention consists of mapping the origin of the carbonate that precipitates as calcium carbonate scale in the production column through the addition of calcite impregnated with chemical tracers in viscous gel-based mattresses. Thus, through this invention it is possible to map whether the tracer added to the calcite is gradually released into the water present in the produced fluid, which can be monitored through chemical analyzes of the water produced. This is due to the fact that when the produced water, together with the oil from the well, passes through the calcite, deposited inside the reservoir during the operation to combat circulation loss, dissolution reaction of the calcite by the produced water will occur, consequently, marking the calcite with a tracer will help to identify the process of formation of calcium carbonate scale. This information will be used to improve the efficiency of the reservoir inhibition process, thus acting to prevent the deposition of calcite in the production column of the well. Thus, it is possible to verify whether the origin of the calcium carbonate in the scale formed in the production column comes from the material injected into the well.

Once the formation of scale in the column has been identified, a descending tool with a wire line equipped with a scraper can be used to remove the sample of calcium carbonate scale at the depth found in the production column, and then be analyzed in the laboratory by dissolving the carbonate sample by grinding the sample with a mortar with a pestle, followed by washing the sample, filtering and measuring the filtrate to check the presence of the tracer. Through the chemical signature that identifies the presence of tracer, thus being able to confirm the origin of this scale. Once this occurrence is confirmed, it is possible to plan ways to mitigate scale formation through material to combat circulation loss, thus avoiding production losses associated with scale formation. For example, it is possible to recommend the addition of scale inhibitors to loss-combating mattresses, as a way of preventing scale generated by calcite used to combat circulation loss during the well construction phase.

In a first embodiment of the invention, the present invention refers to the composition for identifying the origin of scale comprising a mixture of calcite with different particle sizes encapsulated in a chemical tracer with a viscous gel-based mattress.

In the present invention, chemical tracers of non-radioactive compounds, iodides, bromides, alkali metal halides, such as potassium iodide and potassium bromide, are used.

Additionally, the calcite (limestone) used in the present invention is found in concentrations of 15 to 25 lb/bbl, preferably 20 lb/bbl; and can have different grain sizes, such as micronized limestone (2 to 44 μm); fine limestone (2 to 74 μm), medium limestone (74 to 800 μm) and coarse limestone (800 to 5600 μm); being obtained through rock mining.

The mass of calcite is a function of the amount necessary to contain the circulation loss in the well. Therefore, the amount of calcite that will be used in the present invention to combat loss of well circulation can vary from 300 kg to 1000 kg, depending on the well. As it varies from 300 kg to 1000 kg, the amount of tracer will be, respectively, 3 kg to 50 kg.

Said viscous mattress composition used in the present invention comprises:

- 2.5 bbl/m of perforation, with a minimum of 60 bbl pumped per treatment;
- antifoam of 0.05 to 0.15% v/v, preferably 0.1% v/v, where the antifoam belongs to the category of polydimethylsiloxanes, fluorosilicones, polyglycols;
- xanthan gum as viscosifier≥1.5 lb/bbl;
- HPA (hydroxypropyl starch) as filtrate controller of 7 to 9 lb/bbl, preferably 8 lb/bbl;
- magnesium peroxide as breaker at a range of 0.5 to 1.5 lb/bbl, preferably 1 lb/bbl; where this is used to break the viscosity of the gel after a period of contact, thus reducing the viscosity of the gel, thus avoiding the formation of damage to the reservoir, as the gel without viscosity will be produced more easily together with the oil; and
- completion fluid as QSP diluent (sufficient amount) for the preparation and/or displacement of the viscous gel.

In a second embodiment of the invention, the present invention also refers to the process for preparing said composition for identifying the origin of scale comprising the following steps:

a. adding chemical tracer to calcite through processing of the material;
b. placing the calcite in a tank, where it will remain for 2 to 4 hours for the tracer to be adsorbed by it;
c. drying the calcite impregnated with tracers;
d. preparing the viscous mattress in a batch mix tank (12); and
e. adding the calcite added with tracer to the viscous mattress in the batch mix tank (12).

In step (b), the calcite remains in the tank long enough to adsorb the tracer, between 2 and 4 hours. Under these conditions, approximately 1 to 5% of tracer is adsorbed. Drying the impregnated calcite as described in step (c) can be carried out using a conveyor drying system.

In step (d) where the viscous mattress is prepared, 2.5 bbl per meter of perforation is used, with a minimum of 60 bbl per operation and a mixture of fine limestone (2 to 74 μm), medium limestone (74 to 800 μm), at a concentration of 15 to 25 lb/bbl each (preferably 20 lb/bbl). When the previous composition is not effective in reducing fluid loss, coarse limestone (800 to 5600 μm) can also be used at the preferred concentration of 20 lb/bbl.

Preferably, the tracer adsorption step to calcite as described in step (b) can be carried out in a vacuum chamber, according to the following steps:

- placing the calcite inside the vacuum chamber;
- promoting a vacuum inside the vacuum chamber in a range of 5 to 10 mm Hg;
- opening the supply of the aqueous tracer solution into the vacuum chamber;
- waiting to complete the volume necessary to cover the calcite mass inside the vacuum chamber;
- waiting 2 to 4 hours for the tracer to adsorb on the calcite;
- removing excess tracer from the vacuum chamber using conical equipment that separates the liquid that was not absorbed by the calcite (such as a separation funnel) or through a conveyor drying system;
- transferring the calcite added with the tracer to a bench for drying under STP conditions (normal temperature and pressure conditions);
- waiting for the calcite to dry: between 4 and 8 hours; and
- promoting the bagging of dry calcite in bags of 25 to 50 kg.

The main advantage of using vacuum in the impregnation of tracer to calcite is the increase in the amount of tracer to calcite, since due to the removal of air present in the empty spaces of the calcite, the tracer has a greater ability to penetrate the calcite grains. The increased efficiency of filling the calcite grains with the tracer provides a greater volume of tracer in the calcite inside the reservoir, thus enabling monitoring of the origin of the scale formation within the production column of the well.

In a third embodiment of the invention, the present invention refers to the process for identifying the origin of scale using a composition comprising a mixture of calcite with different particle sizes encapsulated in a chemical tracer with a viscous gel-based mattress comprising the following steps:

- pumping the composition containing viscous mattress with calcite added with tracer to the production well to combat circulation loss;

moving the viscous mattress with calcite added with tracer, with drilling fluid into the interval that presents circulation loss;

evaluating the loss flow to check whether the loss has been eliminated; and if it is necessary, repeating the procedure until the loss is eliminated.

In a fourth embodiment of the invention, the present invention further comprises the use of said composition to identify the source of calcium carbonate scale in a well.

Below, without limiting the inventive scope, an example of embodiment of the present invention will be defined.

Example of Implementation

The incorporation of the tracer into calcite can be carried out by immersing the calcite in the tracer solution in an appropriate tank (1) for a certain time in a range of 3 to 6 hours, for absorption of the tracer by the calcite. The added amount of chemical tracer can be in the range of 1 to 5% in relation to the mass of calcite to be used. This addition of the tracer to the calcite can be carried out during the processing of the material, that is, at the end of the manufacturing process. Therefore, the calcite in its different particle sizes (fine, medium and coarse) can be placed in a tank (1), where it will remain for a certain time (between 3 and 6 hours) for the tracer to be absorbed by it, then the impregnated calcite is dried, that is, the excess liquid from the calcite is removed.

This tracer-encapsulated calcite will be made available to be loaded onto the drilling rig. The calcite encapsulated with the chemical tracer will be used during the preparation of the mattress to combat circulation loss. In the bacth mix equipment (12), the gel-based viscous mattress will be prepared in a volume ranging from 40 to 80 BBL (1 bbl=159 liters), in accordance with the procedure for combating loss in the well. Calcite impregnated with tracer will be added to this viscous mattress, then this mattress consisting of the volume of viscous gel with calcite will be pumped by a triplex pump (2) into the well and moved with completion fluid until this mattress is positioned in the well interval where circulation loss is occurring. In this way, it is possible to generate a plug in the reservoir to reduce or eliminate circulation loss, if necessary. If the loss is not mitigated, a new gel-based viscous mattress can be pumped in to supplement the plugging, and this is repeated until the loss is eliminated.

Therefore, the present invention contributes to the formulation of studies to verify the origin of scale in the production columns of oil wells, which allows the development of technologies to prevent oil production losses associated with the formation of scale in subsea production system equipment. By identifying the possible components of the injected fluids (drilling and combating loss), which participate in the generation of mixtures with a high potential for scale formation when mixed with aquifer water, scale formation due to the use of these materials, whether by replacing them or developing treatments for these materials.

Consequently, the present invention has the following advantages:

Avoids financial losses associated with lost production.

Avoid interventions with probes during the field development phase.

Reduces the need for operations with stimulation boats (which cost an average of US$ 9,000,000.00) to pump scale-removing solutions from the well production column and to carry out inhibitor squeeze operations. The advancement of this study will allow the development of technologies to increase the efficiency of scale control. This reduces the risk associated with disconnections of the pumping system of the stimulation boats and the possibility of chemical leaks into the sea.

Improves the guarantee of production flow by helping to avoid the early formation of scale, which increases well productivity time without the need for intervention, thus avoiding production losses associated with scale.

Reduces $CO_2$ emissions due to the reduction in the need to use a WSSV (Well Stimulation Support Vessel) type vessel to carry out scale removal and inhibitor squeeze operations.

Collaborates in maintaining the payment of oil royalties in order to promote the maintenance of production and avoid production losses.

Contributes to improving scale management, thus increasing the efficiency of reservoir management in the fields where this technology is applied.

The technology can be applied in the areas of well construction, in the drilling and/or completion phases, as a way of helping to plan the mitigation of scale formation in advance. Through the development of technologies, to prevent the material used as a buffer, in processes to combat the loss of fluid circulation, from contributing to the formation of scale in subsea production equipment. With this technique, it will be possible to collaborate with the areas of reservoir management, scale management and elevation and drainage, ensuring efficiency and production flow.

In this way, the present invention guarantees the understanding of the origin of the scale in relation to the calcite used to combat loss, thus contributing to the prevention of chemical inhibition in the reservoirs of the producing intervals, already in the drilling phase.

The invention claimed is:

1. A composition for identifying an origin of calcium carbonate scale, comprising a mixture of calcite with different particle sizes encapsulated in a chemical tracer with a gel-based mattress.

2. The composition according to claim 1, wherein the calcite has a weight of 300 kg to 1000 kg and the chemical tracer has a weight of 3 kg to 50 kg.

3. The composition according to claim 1, wherein the chemical tracer comprises one or more compounds selected from non-radioactive compounds, iodides, bromides and halides of alkali metals.

4. The composition according to claim 3, wherein the halides of alkali metal are selected from potassium iodide and potassium bromide.

5. The composition according to claim 1, wherein the calcite with different particle sizes comprises micronized limestone of 2 to 44 μm particle size;

fine limestone of 2 to 74 μm particle size;

medium limestone of 74 to 800 μm particle size; and coarse limestone of 800 to 5600 μm particle size; wherein the calcite is in a concentration of 15 to 25 lb/bbl.

6. The composition according to claim 1, wherein the composition of the gel-based mattress comprises:

2.5 bbl/m of perforation, with a minimum of 60 bbl pumped per treatment;

antifoam of 0.05 to 0.15% v/v, wherein the antifoam is selected from polydimethylsiloxanes, fluorosilicones, and polyglycols;

xanthan gum as a viscosifier≥1.5 lb/bbl;

HPA (hydroxypropyl starch) as a filtrate controller of 7 to 9 lb/bbl;

magnesium peroxide as a breaker at a range of 0.5 to 1.5 lb/bbl; and completion fluid.

7. The composition according to claim 1, wherein a weight of the chemical tracer is 1 to 5% of a weight of the calcite.

8. The composition according to claim 5, wherein the calcite concentration is 20 lb/bbl.

9. A process for preparing the composition as defined in claim 1, comprising following steps:

(a). adding the chemical tracer to the calcite;

(b). placing the calcite in a tank for 3 to 6 hours for the chemical tracer to adsorb into it;

(c). drying the calcite impregnated with the chemical tracer;

(d). adding the calcite impregnated with the chemical tracer to the gel-based mattress in a batch mix tank.

10. The process according to claim 9, wherein in step (b), 1 to 5% of the chemical tracer is adsorbed.

11. The process according to claim 9, wherein step (c) is carried out using a conveyor drying system.

12. The process according to claim 9, wherein step (b) further comprises use of 2.5 bbl per meter of perforation, with a minimum of 60 bbl per operation and a mixture of fine limestone of 2 to 74 μm particle size and medium limestone of 74 to 800 μm particle size, at a concentration of 15 to 25 lb/bbl each.

13. The process according to claim 12, wherein step (b) further comprises use of coarse limestone of 800 to 5600 μm particle size at a concentration of 20 lb/bbl.

14. The process according to claim 9, wherein step (b) is carried out in a vacuum chamber.

15. The process according to claim 14, wherein following steps are carried out in the vacuum chamber:

placing the calcite inside the vacuum chamber;

promoting a vacuum inside the vacuum chamber in a range of 5 to 10 mm Hg;

opening a supply of a solution containing the chemical tracer into the vacuum chamber;

waiting to complete a volume necessary to cover the calcite inside the vacuum chamber;

waiting 2 to 4 hours for the chemical tracer to adsorb on the calcite;

removing excess chemical tracer from the vacuum chamber using conical equipment that separates the solution that was not absorbed by the calcite or through a conveyor drying system;

transferring the calcite impregnated with the chemical tracer to a bench for drying under normal temperature and pressure conditions;

waiting for the calcite to dry for between 4 and 8 hours.

16. A process for identifying the origin of calcium carbonate scale using the composition as defined in claim 1, comprising the following steps:

(i) pumping the composition containing gel-based mattress with calcite impregnated with the chemical tracer to a production well;

(ii) moving the gel-based mattress with calcite impregnated with the chemical tracer, with a drilling fluid into an interval that presents circulation loss;

(iii) evaluating a flow for a loss, to check whether the loss of the flow has been eliminated; and (iv) repeating steps (i) to (iii) until the loss of the flow is eliminated.

* * * * *